United States Patent
Teiwes et al.

(10) Patent No.: US 7,517,085 B2
(45) Date of Patent: Apr. 14, 2009

(54) METHOD AND APPARATUS FOR EYE TRACKING LATENCY REDUCTION

(75) Inventors: Winfried Teiwes, Teltow (DE); Horia Grecu, Teltow (DE)

(73) Assignee: SensoMotoric Instruments GmbH, Teltow (DE)

( * ) Notice: Subject to any disclaimer, the term of this patent is extended or adjusted under 35 U.S.C. 154(b) by 607 days.

(21) Appl. No.: 11/144,212

(22) Filed: Jun. 2, 2005

(65) Prior Publication Data
US 2005/0273185 A1    Dec. 8, 2005

(30) Foreign Application Priority Data
Jun. 2, 2004    (EP)    ................... 04013016

(51) Int. Cl.
*A61B 3/14* (2006.01)
(52) U.S. Cl. ...................... 351/209; 351/246
(58) Field of Classification Search ................ 351/206, 351/209, 210
See application file for complete search history.

(56) References Cited

U.S. PATENT DOCUMENTS

| | | | |
|---|---|---|---|
| 5,517,021 A | 5/1996 | Kaufman et al. | |
| 6,120,461 A | 9/2000 | Smyth | |
| 6,959,450 B1 * | 10/2005 | Ritter et al. | 725/133 |
| 7,206,435 B2 * | 4/2007 | Fujimura et al. | 382/117 |
| 2008/0024598 A1 * | 1/2008 | Perlin et al. | 348/55 |

* cited by examiner

*Primary Examiner*—Jordan M. Schwartz
(74) *Attorney, Agent, or Firm*—Marger Johnson & McCollom, P.C.

(57) ABSTRACT

A method for enhancing the performance of an eye position measurement system, said method comprising:
  based on a measurement of past eye positions, calculating a prediction of a future eye position;
  using said calculated prediction of a future eye position for reducing the latency effect of said eye position measurement system.

9 Claims, 3 Drawing Sheets

METHOD AND APPARATUS FOR EYE TRACKING LATENCY REDUCTION

FIELD OF THE INVENTION

The present invention relates to a method and an apparatus describe for reducing the latency of an eye tracking system, in particular for an eye tracking system used in connection with a retinal diagnostic or surgical device.

BACKGROUND OF THE INVENTION

Eye tracking systems are used in a variety of applications, mostly in the medical field like in connection with systems for surgery or diagnosis. An eye tracking system typically senses the eye in real-time using either photodiodes or camera and based on signal or image processing methods then estimates the motion of the eye to enable a compensation of the motion to be carried out at the diagnostic or surgery device to enable proper operation of this device and to avoid positioning errors.

Once an image of an eye has been taken it takes some time (processing time) until based on the image processing algorithm the position of the eye has been determined, this time is referred to as "latency". If based on the eye position thus determined some feedback is to be given to a surgical or diagnostic device and if based on this feedback some position compensation should be carried out then the time necessary to carry out this compensation (e.g. by movement of the device or some of its parts) also contributes to the latency of the overall system.

One concrete example where such an eye tracking system is used in connection with a diagnostic or surgical device is a system for retinal video tracking for an Optical Coherence Tomography (OCT). An OCT system works similar to an ultrasound imaging device except that instead of ultrasound it uses infrared (IR) light which is emitted, reflected by the retina and then based on the reflected light and image processing methods a diagnostic image is obtained. Eye tracking with low latency effects can be implemented to ensure repeatable diagnostic images despite eye movements during image acquisition. The combined eyetracking OCT device then can be used for repeatably measuring thickness and structure of the retinal layers over time. Simarly, eye tracking with low latency effects is required for compensating eye movement during laser refractive surgery.

In such applications a measurement/correction device is operating at precise locations on the eye. In order to compensate the inherent eye-position changes, an eye-tracking system is usually employed. The eye-tracking system measures the eye-position at fixed intervals and communicates the data to the effectors system. The time elapsed between the measurement moment and the end of effectors system adjustment to the new position is defined as latency. The latency time includes the time required for performing the measurement, the communication time and the effectors (e.g. mirrors) adjustment time.

The latency time translates to an eye position uncertainty, called dynamic uncertainty, due to fact that eye movement in the elapsed time is unknown, and consequently it is desired to minimize the latency effects. It is therefore the object of the present invention to provide a method and an apparatus which reduces the latency effects of an eye tracking system.

SUMMARY OF THE INVENTION

According to an aspect of the invention there is provided a method for enhancing the performance of an eye tracking system, said method comprising:
based on a tracking of past eye movements, calculating a prediction of a future eye position;
using said calculated prediction of a future eye position for reducing the latency effect of said eye tracking system.

By calculating a forecast for an eye movement based on a record of eye movements in the past there is provided the possibility for reducing the latency of an eye tracking system. Such an eye tracking system may then be used in connection with or be integrated in an ophthalmic diagnostic/surgical device which then yields an improved accuracy.

Such a method or system according to an embodiment of the invention allows reduction of the dynamic uncertainty based solely on the eye position data as delivered by the eye-tracking system. It therefore reduces the apparent latency time not by modifying the physical time required, but by modifying the effects of it in the overall system.

According to one embodiment the prediction interval corresponds to the processing time required by said eye tracking system to determine the position of the eye. This ensures that the delay introduced by the processing is compensated According to one embodiment the prediction interval corresponds to the processing time required by said eye tracking system to determine the position of the eye plus the compensation time of an ophthalmic device performing surgery and/or diagnosis. This ensures that in an overall system for diagnosis/surgery any necessary time for mechanical position compensation is taken into account.

According to one embodiment the prediction is generated for different prediction intervals which are submultiples of the eye-tracking period. This ensures that the system can provide arbitrary super-sampling rate of eye motion.

According to one embodiment a predicted position is compared with a later determined actual position to monitor the quality of said prediction. This keeps the system up to date about current prediction quality and may be used to update the prediction mechanism.

According to one embodiment there is provided a method of predicting a future movement of an eye position, said method comprising:
comparing a sequence of eye positions with data representing typical patterns of eye movements;
based on said comparison, calculating a prediction for a future eye position.

The method can be used in connection with an eye tracking system to reduce its latency, it may also be used at other systems where a prediction of an eye movement may be useful. E. g. it may be used in connection with any system which measures the position of an eye. One such example could be a system which monitors the field of view of a person in order to monitor whether the line of sight reaches an area where the person should not look at, e.g. if a driver or a pilot looses attention and looks around.

According to one embodiment there is provided a database containing a plurality of datasets representing sequences of typical eye movements; and
based on a past eye movement from a certain time in the past up to the present, there is picked the dataset among the plurality of datasets which predicts best the future eye movement.

According to one embodiment said datasets are FIR filters.

According to one embodiment there is calculated a cost function to evaluate the quality of the prediction based on the predicted value and the actually measured value, and the selection of said dataset is adapted based on said cost function. This enables to take into account a change in prediction quality.

According to one embodiment the method further comprises:
- calculating a performance measurement which indicates for a certain dataset its prediction performance over time;
- selecting the dataset used for prediction based on said performance measurement; and
- updating said performance measurement based on a comparison between the predicted value and the actually measured position.

The performance measurement takes into account the performance over the past and also additionally an instantaneous change of the prediction quality which is expressed by the cost function.

According to further embodiments there are provided an eye tracking systems corresponding to and implementing the methods according to embodiments of the invention.

Furthermore there is provided a computer program comprising code for enabling a computer to carry out methods according to embodiments of the invention.

DETAILED DESCRIPTION

An embodiment of the present invention is now explained in connection with FIG. 1. A camera (e.g. a CCD camera) 110 takes video images of an eye 100, and the images are fed to a computer 120. Such an arrangement is equal to a classical eye tracking system and it may also be applied to the present invention. In the conventional eye tracking system, based on the images captured the computer 120 "tracks" the eye movement, e.g. by comparing the position of some "landmarks" in the momentary image with the position in the previous image to thereby "track" the movement of the eye. Based on the tracked actual position a feedback signal may be determined which then is used to carry out a position compensation at a surgical or diagnostic device (not shown in FIG. 1).

According to an embodiment of the present invention camera 110 captures a sequence of images of the eye up to the present, e.g. of the most recent several tens of seconds. The computer 120 then analyzes this sequence of movements which occurred in the past and based on the analysis then calculates a prediction or forecast which gives the most likely position which the eye 100 will assume in the future based on the positions in the past.

According to one embodiment the forecast relies on some knowledge about how eyes "typically move", one can say that the method used compares the measured past eye movements in some recent moments with the knowledge about typical eye movements in general, and based on that comparison an estimation is made as to what might be the most likely position of the eye after the measured sequence and based on the measured sequence. This then gives a prediction of a future eye position.

According to one embodiment the invention makes use of is the fact that the eye movements are not a completely random process. Especially the large and fast movements are known to obey certain characteristics that are very specific to eye motion. Therefore, a model of the eye motion can be developed and based on the particular eye motion history— the future trajectory of the observed eye is forecasted. According to one embodiment the forecasting time horizon is designed to be equal to the measured latency of the entire system—including measurement time, communication time, effectors time.

Figure 1:
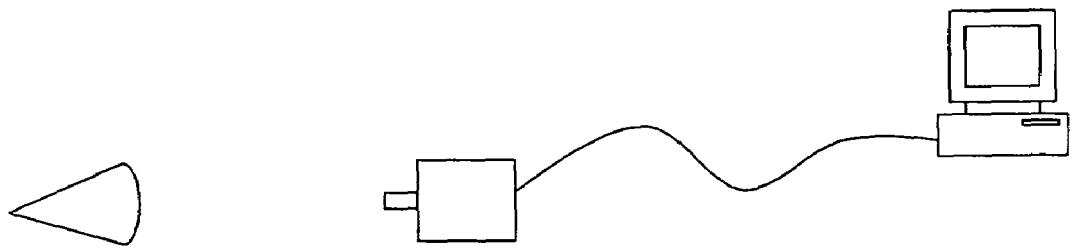
FIG. 1 schematically illustrates a configuration for implementing an embodiment of the present invention.
Figure 2:
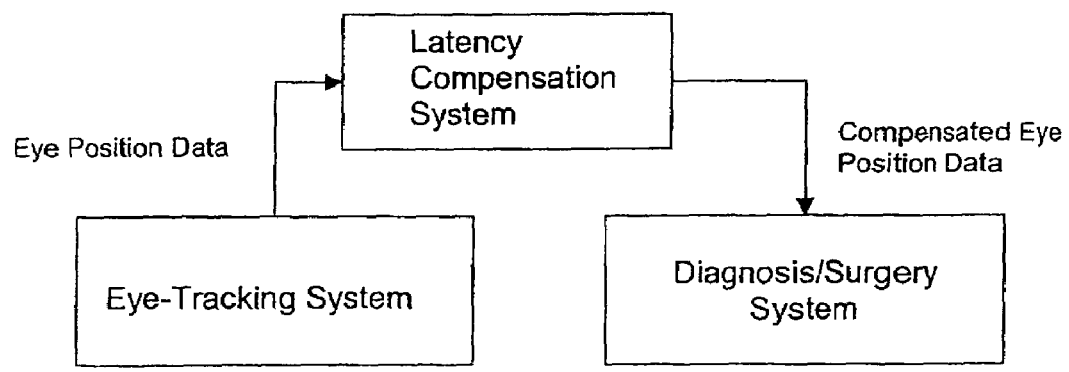
FIG. 2 schematically illustrates a feedback loop according to an embodiment of the invention.

The general diagram of how such a latency compensation system according to one embodiment fits into a classical eye tracking system and a surgical/diagnostic system is shown in FIG. 2. The conventional eye tracking system (as shown in FIG. 1) provides position data which is then used by the latency reduction system to calculate a position forecast. This forecast is then fed to the diagnosis/surgery system to be used as a feedback for position compensation.

For calculating the forecast according to one embodiment there is made use of an "eye motion model" which is representative of typical eye motions and which can be used as a basis for the forecast. According to one embodiment this model is based on observation of typical eye motions base.

Figure 3:
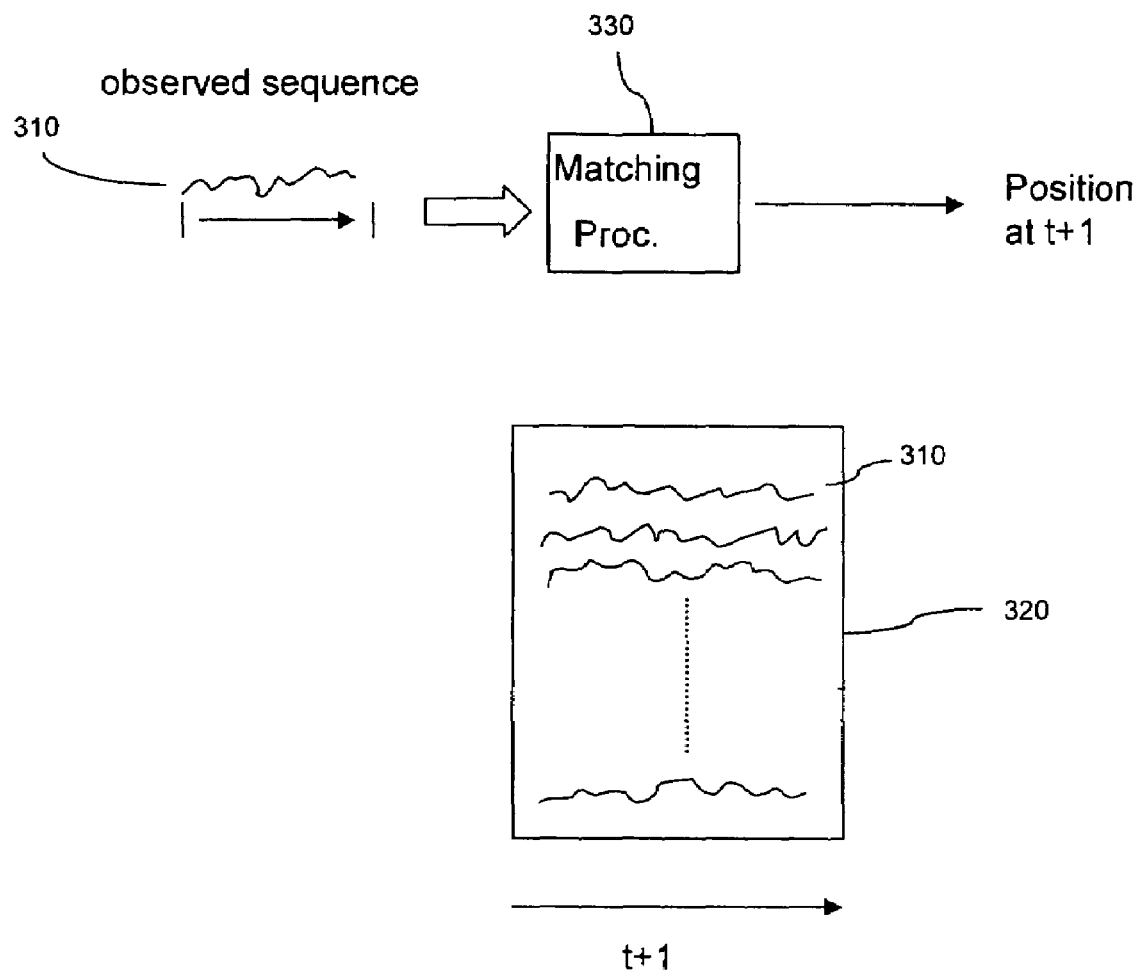
FIG. 3 schematically illustrates the operation of an embodiment according to the present invention.

According to one embodiment there is a model (or knowledge database) which for a certain sequence of past movements gives the most likely future movement. This can be done by a method as schematically illustrated in FIG. 3. The eye movement is measured over a time t to yield the sequence 310 of eye positions based on which a prediction of the eye position at t+1 should be made. In the knowledge database 320 there are stored several sequences 310' which represent typical eye movements over a time t+1, they represent an a priori knowledge about typical eye movements which has been established in advance by measuring a lot of sequences 310' and determining "typical sequences". The actual measured sequence 310 is then in the matching processor 330 compared with all the sequences 310' stored in the knowledge base 320 and based on this comparison the sequence 310' which matches best with the actually measured sequence is determined by calculating some measure representing the closeness between the actual sequence and the different model sequences 310'. Based on this sequence 310' which gives the best representation (the "best model") then the forecast of the position of the eye at time t+1 is determined.

According to a further embodiment in knowledge base 320 there are not stored actual sequences of eye movements but rather some (mathematical) models which enable a prediction of a future eye position based on past measured eye positions. Such a model may e.g. a vector representing a FIR filter which may be used for prediction of a future position, and each such a vector yields then a certain prediction based on the observed sequence. The prediction then for each vector (or model) is evaluated using some cost function, and the set of models together with their corresponding cost function values may then be regarded as "observed eye motion model" because it is continuously observed with respect to its performance.

According to one embodiment the Observed Eye Motion Model itself may evolve based on a combination of a-priori knowledge delivered by a general eye motion model and by the difference between observed motion and predicted motion. The prediction quality is continuously monitored as the difference between the predicted value for moment t+1 and the measured value at that particular moment, and based thereupon the models are updated by updating their corresponding (global) performance measurement which is influenced by the monitored instantaneous performance (a comparison of the predicted and the actually measured value at a certain time). By calculating a global performance measurement based on the instantaneous performance and the performances of the individual models over the past a good balance can be achieved between the capability to adapt to changes and taking into account past successful predictions to a suitable extent.

According to one embodiment the prediction is performed independently on the x and y direction. Hence there is applied two times the same strategy for predicting a 1-dimensional signal. In the following reference will be made only to one of the directions (say e.g. x), the skilled person will readily understand that for the other (say e.g. y-) coordinate the method can be applied likewise.

The prediction according to one embodiment can be performed by an adaptive linear model approach. The main idea of the method is to build a set of linear models expressed as FIR (Finite Impulse Response) filters that best explain the data in a number of patient recordings. Once the model set is built, the procedure to obtain the prediction at a current step can be the following:

a. Pick the current best model, according to its global performance.
b. Output the prediction value as the result.
c. Evaluate the prediction based on each linear model and store them.
d. Update the global performance of each model by comparing the last prediction with the current measured position.

Figure 4:
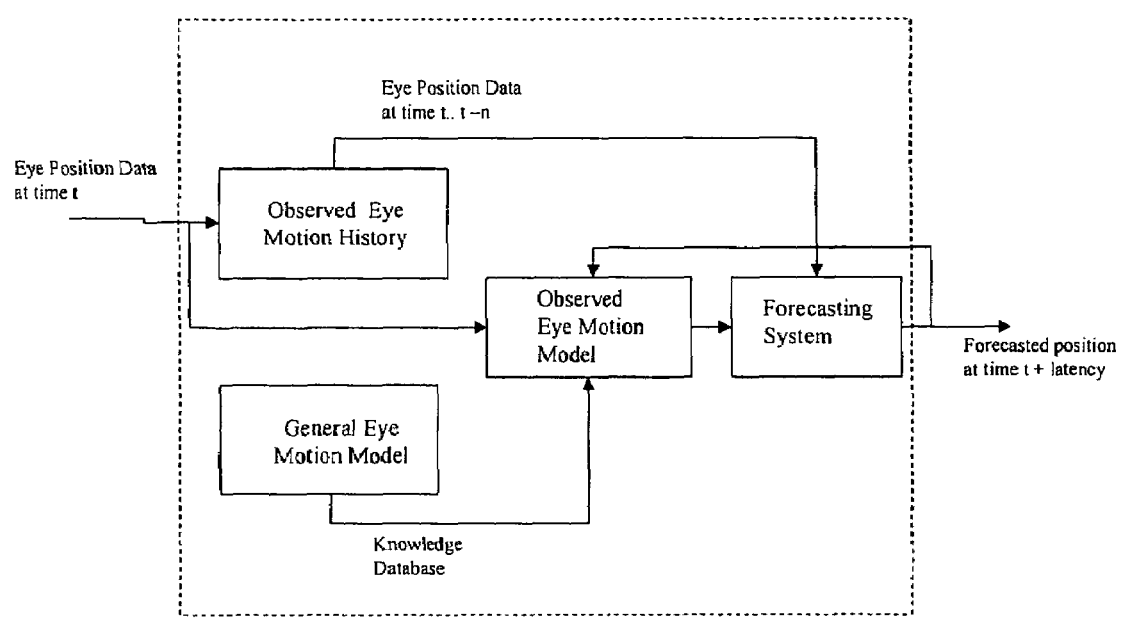
FIG. 4 schematically illustrates a further embodiment of the invention

FIG. 4 schematically illustrates the flow of information according to the present embodiment. Based on the observed eye motion history and the knowledge database there is picked an eye motion model among the observed eye motion models which is the one from the models in the database which has the best overall performance at the instantaneous moment. The observed eye motion history and the picked model with the best global performance then are used to forecast a position at time t+1 (=t+latency). The actual value at t+1 is then measured and compared with the predicted value, and based thereupon an update (if necessary) of the observed eye motion model (the models and their corresponding global performances) is carried out. If the performance of another model in the database turns out to be better then this model will then be chosen as the eye motion model for further forecasting.

In the following the individual steps according to a further embodiment will now be explained in somewhat more detail.

Eye motion sequences are represented respectively by FIR models, and each FIR model M is represented by a vector of numbers M=[m0, m1, . . . m5]. The dimension of 5 here is chosen exemplary only, other dimensions can be used as well. The output of the model prediction is simply the convolution of the vector M with the vector of past pupil values:

Pupil $(t+x)=m0*$Pupil $(t)+m1*$Pupil $(t-1)+m2*$Pupil $(t-2)+\ldots m5*$Pupil$(t-5)$ While simple, linear models like this are known to be able to model a very large number of functions.

The performance of each model is based on the cost function associated with each error, which is given by the relation:

Cost=max(min(err^2, UpperBound^2), LowerBound^2)−LowerBound^2 where UpperBound=1.2 and LowerBound=0.2, represent the maximum and minimum significant squared error levels.

That means that errors of less than 0.2 pixels in absolute value will be ignored, and errors of more than 1.2 pixels will be equally considered.

The performance is obtained as an exponential averaging by the equation

Performance$(t+1)=$Performance $(t)+$updateFactor$*$Cost$(t)$ where t represents the time instant and updateFactor=0.005 is the parameter that controls the adaptability of the system. A large value of updateFactor, will force the system to 'forget' quicker the past behavior and reciprocally.

In the following computing of the models according to an embodiment of the invention will be described in more detail.

It should be noted that according to an embodiment all models of the set are tested simultaneously for each input and the best-fit model exemplar is picked up, at each instant, to represent the likely eye motion. Hence, the computational time is directly proportional to the number of models in the set. According to the present embodiment there is therefore looked for a method to establish a low enough number of models that can explain well any eye motion trajectories. For this purpose there is followed a bottom-up approach:

First, there is built a large number of models that can clearly explain well the training examples
Second, the very similar looking models are grouped together and replaced by a single model, usually called the prototype of the group. Such action falls under the name of 'clustering' and is treated considerable in the literature and known to the person skilled in the art.

As an exemplary reference is made to:

a. A. K. Jain, M. N. Murty, and P. J. Flynn, *Data clustering: a review*, ACM Computing Surveys, 31(3): 264-323, 1999
b. Richard. O. Duda, *Pattern Classification*, Wiley-Interscience (2nd edition), 2000
c. T. Kohonen, *Self-Organizing Maps*, Springer, New York 1997.

The models set used in the present embodiment consists of 16 linear model prototypes of dimension 6. This means that the last 6 values of the pupil position are used in the computation of the future predicted position. To obtain the 16 filter prototypes, the following procedure can be employed:

1. A number of 50 recordings are used to build a sequence of about 70000 pupil positions.
2. By random sampling, a number of 200 virtual sequences of length 1500 are produced
3. For each virtual sequence the optimal LSE (least square error) linear model (of size 6) is computed using SVD based algorithm. SVD (Singular Value Decomposition is a standard technique for this purpose and well known to any person skilled in the art.
4. The set of 200 linear models—the large set of models— is clustered in 16 classes using Fuzzy C-Means algorithm. A detailed description of this algorithm which is well known to any skilled person is for example found in:
a. J. C. Bezdek, *Pattern Recognition with Fuzzy Objective Function Algorithms*, Plenum Press, New York 1981.
b. James C Bezdek, James Keller, Raghu Krisnapuram, and Nikhil R Pal, *Fuzzy Models and Algorithms for Pattern Recognition and Image Processing*, Kluwer Academic Publishers, 1999
c. Uri Kroszynski and Jianjun Zhou, *Fuzzy Clustering Principles, Methods and Examples*, IKS, December 1998

5. The prototype of each of the 16 classes represents the set of linear models.

Since the SVD algorithm and Fuzzy C-Means algorithms are well known to any person skilled in the art and extensively described in the literature they are not described here in detail.

The best model for the current prediction is picked at each time instant by $$Mbest(t)=argmax(Performance(t))$$

The Mbest(t) model is then used as described above for computing the predicted pupil position.

It should be noted that Mbest(t) is the index of the model and not the model itself (i.e. not the vector)

With respect to the foregoing description and the components shown in FIG. 4 the following correspondence can be noted.

The General Eye Motion Model is represented by the set of 16 filter models of size 6, obtained following the procedure described above.

The Observed Eye Motion Model is represented by the vector of performance values associated with each model: Performance(t)=[M1Perf(t), M2Perf(t), . . . M16Perf(t)]. As noted, the performance vector is evolving in time. The evolution of this vector over time has been described before.

The Observed Eye Motion History is the vector of the last 6 positions of the eye $$Motion\ History=[Pupil(t)Pupil(t-1)Pupil(t-2)Pupil(t-5)]$$

The Forecasting System selects the best model (the model having the best global performance) and computes the forecasted position using this model as described in the foregoing.

The skilled person will understand that the methods, apparatuses and systems according to embodiments of the invention as described hereinbefore may be implemented by a configuration comprising a standard video camera, and a standard computer as schematically illustrated in FIG. 1. The computer may be equipped with some standard software for video capturing, and as far as the foregoing description and the claims relate to modules or components implementing the invention the skilled person will readily understand that they may be implemented either in hardware or in software in connection with the basic configuration shown in FIG. 1. Based on the foregoing description the skilled person will be readily able to adapt the system shown in FIG. 1 by suitable programming of the computer and its components to perform the functions described in connection with the embodiments of the present invention.

It is further to be understood that the foregoing embodiments are described as exemplary embodiments only, and that modifications to these embodiments are possible to the skilled person and should therefore ce considered as lying within the scope of the invention. E.g. in addition to an OCT device the invention may be applied to any surgical or diagnostic device. Moreover, apart from the area of surgical and diagnostic devices the present invention may be applied in the field of eye tracking and in eye tracking devices in general.

Moreover, the invention may not only be applied to eye tracking, be it video-based or non-video-based, but it may be applied to any method or device used for measuring or determining the position of an eye, be it for tracking of the movement of the eye or for any other reason or purpose.

What is claimed is:

1. A method for enhancing the performance of an eye position measurement system, said method comprising:
based on a measurement of past eye positions, calculating a prediction of a future eye position;
using said calculated prediction of a future eye position for reducing a latency effect of said eye position measurement system;
using said prediction of a future eye position in connection with a system for ophthalmic surgery and/or diagnosis for compensating for an eye movement, wherein said calculating a prediction of a future eye position includes a prediction interval corresponding to a processing time of said eye position measurement system to determine the position of the eye and a compensation time of an ophthalmic device performing surgery and/or diagnosis.

2. The method of claim 1, wherein the prediction is generated for different prediction intervals which are submultiples of an eye-tracking period.

3. The method of claim 1, further comprising:
comparing a predicted position with a later determined actual position to monitor the quality of said prediction.

4. The method of claim 3, further comprising:
adapting a prediction calculation used for prediction based on said monitoring result.

5. An apparatus for ophthalmic surgery and/or diagnosis for compensating for an eye movement, said apparatus comprising:
an eye position measurement system including:
a module for measuring past eye positions; and
a module for calculating a prediction of a future eye position, wherein
said calculated prediction of a future eye position is used for reducing the latency effect of said eye position measurement system and wherein said prediction of a future eye position includes a prediction interval that corresponds to a processing time of said eye position measurement system to determine the position of the eye plus a compensation time of an ophthalmic device performing surgery and/or diagnosis.

6. The system of claim 5, wherein the prediction is generated for different prediction intervals which are submultiples of an eye-tracking period.

7. The system of claim 5, further comprising:
a module for comparing a predicted position with a later determined actual position to monitor the quality of said prediction.

8. The system of claim 7, further comprising:
adapting a prediction calculation used for prediction based on said monitoring result.

9. A computer comprising a computer program for enhancing the performance of an eye position measurement system, said computer program comprising:
computer program code for, based on a measurement of past eye positions, calculating a prediction of a future eye position;
computer program code for using said calculated prediction of a future eye position for reducing the latency effect of said eye position measurement system; and
computer program code using said prediction of a future eye position in connection with a system for ophthalmic surgery and/or diagnosis for compensating for an eye movement, wherein said prediction of a future eye position includes a prediction interval that corresponds to a processing time by said eye position measurement system to determine the position of the eye plus a compensation time of an ophthalmic device performing surgery and/or diagnosis.

* * * * *